| United States Patent [19] | [11] | 4,122,193 |
|---|---|---|
| Scherm et al. | [45] | Oct. 24, 1978 |

[54] DRUGS OR MEDICINES FOR INFLUENCING THE CENTRAL NERVOUS SYSTEM

[75] Inventors: Arthur Scherm, Bad Homburg; Dezsö Peteri, Hammersbach, Marköbel, both of Germany

[73] Assignee: Merz & Co., Germany

[21] Appl. No.: 352,893

[22] Filed: Apr. 20, 1973

[30] Foreign Application Priority Data

Apr. 20, 1972 [DE] Fed. Rep. of Germany ....... 2219256
Apr. 12, 1973 [DE] Fed. Rep. of Germany ....... 2318461

[51] Int. Cl.$^2$ .......................... A01N 9/20; A01N 9/24
[52] U.S. Cl. .................................. 424/330; 260/501.1; 260/563 P; 424/316
[58] Field of Search ..................... 424/325; 260/563 P

[56] References Cited

U.S. PATENT DOCUMENTS

| 3,391,142 | 7/1968 | Mills et al. ...................... 260/563 X |
|---|---|---|
| 3,789,073 | 1/1974 | Narayama et al. ............. 260/563 X |
| 3,929,888 | 12/1975 | Cashin et al. .................... 260/563 X |

FOREIGN PATENT DOCUMENTS 1,545,327  9/1970  France .................................. 260/570.7

OTHER PUBLICATIONS

Eberhard et al., "Chemical Abstracts," vol. 71, p. 235, Section No. 38444b (1969).
Wagner et al., "Synthetic Organic Chemistry," p. 664 (1953).

*Primary Examiner*—Robert V. Hines
*Attorney, Agent, or Firm*—Gordon W. Hueschen

[57] ABSTRACT

Certain 1,3,5-trisubstituted adamantane compounds having central nervous system activity, especially anti-Parkinsonism activity, method of preparing same, and pharmaceutical compositions thereof, method of influencing the central nervous system therewith.

4 Claims, No Drawings

DRUGS OR MEDICINES FOR INFLUENCING THE CENTRAL NERVOUS SYSTEM

The present discovery concerns drugs which influence the central nervous system. The drugs of the invention are particularly well-suited for the treatment of Parkinson's disease. Furthermore, the discovery concerns a method of production of the involved drugs.

It is known that 1-amino-adamantane can effect the central nervous system of humans and animals, and it has accordingly been used in the treatment of Parkinson's disease.

Furthermore, it is known that 1-amino-adamantane and its N-alkyl or N-cyclohexyl derivatives can be produced through transposition from 1-halogen-adamantane with the appropriate urea at high temperatures. The compounds obtained in this manner are useful pharmaceuticals for prophylaxis against influenza virus infection.

Also, from a treatise in the publication "Journal of Medical Chemistry" 6, 6 (1963), pp. 760–763, a method of preparation of 1-amino-3,5-dimethyl-adamantane is known. The treatise describes, among other things, the testing of the 1-amino-3,5-dimethyl-adamantane, and also a similarly based compound with the side chain $ArSO_2NHCONH-$, as a blood sugar level depressant. Therein it was determined that this medicine possesses no blood sugar depressant properties.

The proposition of the present investigation is to discover new medicines which influence the central nervous system, especially for the treatment of Parkinson's disease.

The drugs concerned include as active agents 1,3,5-trisubstituted-adamantane compounds having the following structural formula:

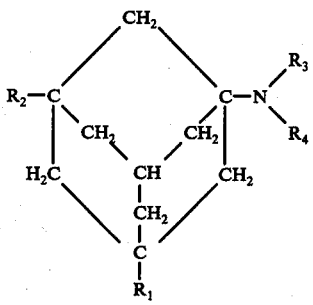

in which the
  $R_1$ and $R_2$ radicals represent lower straight-chain or branched alkyl groups; the
  $R_3$ radical represents hydrogen, a lower straight-chain, branched, or cyclic alkyl group; and the
  $R_4$ radical represents hydrogen, or a methyl group, or a salt of the compound.

Specific salts are, among others, the hydrochloride, the hydrobromide, or the sulfate. The hydrohalogens are preferred.

Among other compounds belonging to the above group are:
  1-amino-3,5-dimethyl-adamantane;
  1-amino-3-methyl,5-ethyl-adamantane;
  1-amino-3,5-diethyl-adamantane;
  1-amino-3,5-di-isopropyl-adamantane;
  1-amino-3,5-di-n-butyl-adamantane;
  1-N-methylamino-3,5-dimethyl-adamantane;
  1-(N,N-dimethylamino)-3,5-dimethyl-adamantane;
  1-(N,N-dimethylamino)-3,5-diethyl-adamantane;
  1-N-isopropylamino-3,5-dimethyl-adamantane;
  1-(N-methyl,N-n-isopropylamino)-3-methyl,5-ethyl-adamantane;
  1-(N-cyclohexylamino)-3,5-dimethyl-adamantane,
and their salts, such as hydrochloride, hydrobromide, or the sulfate. 1-Amino-3,5-dimethyl-adamantane hydrochloride has proved to be particularly effective.

Compounds of the type described above possess the valuable pharmaceutical properties of influencing the central nervous system of humans and animals. The compounds are especially well-suited for the treatment of Parkinson's disease.

The procedure for the production of the drugs studied from 1,3,5-trisubstituted-adamantane compounds, consists of the following steps:

(a) a 1-halogen-3,5-dialkyl-adamantane of the following structural formula:

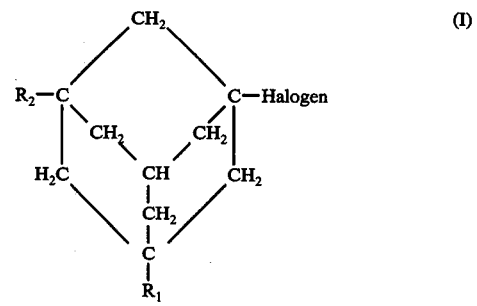

is reacted with a urea of the following structural formula:

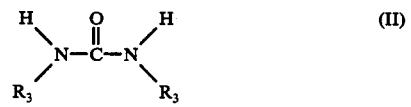

according to a known reaction at an elevated temperature;

(b) conversion of the product of a) to the tertiary amine with formaldehyde and formic acid through transposition at an elevated temperature; and (c) consequent precipitation as a salt from a neutral solution by acidification, in which foregoing formulas the $R_1$ and $R_2$ radicals again represent lower straight-chain or branched alkyl groups, and the $R_3$ radical represents hydrogen, a lower straight-chain, branched or cyclic alkyl group.

As starting materials for the discovered preparation from 1,3,5-trisubstituted adamantane compounds, 1-halogen-3,5-dialkyl-adamantanes proved advantageous. Particularly suitable are 1-chloro-3,5-dialkyl-adamantanes or 1-bromo-3,5-dialkyl-adamantanes, the latter being especially preferred. Starting materials of those kinds are readily obtainable through halogenation, especially bromination, from 3,5-dialkyl-adamantanes. 1-Bromo-3,5-dimethyl-adamantane, which is commercially available, can be used particularly conveniently.

Examples of other investigated starting materials are, for example:
  1-chloro-3,5-dimethyl-adamantane;
  1-bromo-3-methyl,5-ethyl-adamantane;
  1-bromo-3,5-diethyl-adamantane;
  1-bromo-3,5-di-isopropyl-adamantane;

1-bromo-3,5-di-n-butyl-adamantane,
and others.

The ureas used for introduction of the amino- or alkyl-amino group are known compounds. To introduce an unsubstituted amino group, unsubstituted ureas were used. To introduce secondary amino groups, N,N'-substituted amino groups were used. Among the ureas used were:

N,N'-dimethylurea;
N,N'-diethylurea;
N,N'-di-n-propylurea;
N,N'-dicyclohexylurea, and other ureas.

Prepared in the manner of the invention were 1-halogen-3,5-dialkyl-adamantanes, transposed with the suitable urea at elevated temperatures. It proved expedient to perform the transposition with a molar weight excess of the urea. Favorable results were achieved when one part starting material was used for 1.3 to 2.0 parts of urea. In a particularly favorable trial of the discovery being discussed, 1 part of 1-halogen-3,5-dialkyl-adamantane was transposed with 1.5 parts of the selected urea.

The transposition occurs at elevated temperatures. At room temperature, solid reaction compounds, such as 1-bromo-3,5-dimethyl-adamantane, do not transpose with ureas, so the reaction compounds must be heated, at least to the melting point of the mixture. There is an upper limit to the temperature, because at too high a temperature, excessive sublimation of the reaction compounds can occur. The reaction proceeds at sufficient speed and without exceptional loss of yield in the region of 120° to 260° C. Temperatures in the region of 140° to 180° C. are preferred, but even higher temperatures can be used without hesitation.

The transposition between reactants continues essentially to completion. Since heat is released in the reaction, in some cases it is advantageous to place the reactants in an inert solvent to carry away the released heat more easily. In especially large preparations, on the scale of 10 to 100 grams, it proved expedient to perform the transposition in about a 3- to 10-fold amount by weight (based on the sum of the reactants) of an inert solvent. Particularly well-suited are water-insoluble solvents. Diphenyl ether ($C_{12}H_{10}O$) or diphenylene oxide ($C_{12}H_8O$) are representative.

The reaction can be run at atmospheric pressure in an open vessel. It is, however, expedient, especially at high temperatures, to conduct the reaction in a closed vessel to hold the loss of starting materials through sublimation to a minimum.

The reaction proceeds smoothly in general, without requiring exceedingly long reaction times. At higher temperatures, the reaction time is shorter. Conversely, at low temperatures, longer reaction times are necessary. The reaction times depend on the individual 1-halogen-3,5-dialkyl-adamantane and the individual urea. In general, reaction times between 8 and 250 minutes are sufficient, although even longer reaction times are possible. However, as a rule, such prolongation does not produce commensurate improvements in yield. After the transposition, the reaction product is cooled to room temperature, and treated with a considerable excess of water which has been brought to a pH between 3 and 5 by addition of acid. It is advantageous to treat the cooled reaction mixture with neutral water, and to this add, dropwise, concentrated hydrochloric acid until the pH is between 3 and 5 and the desired compound has gone into solution. The insoluble part is filtered off, and the water phase extracted at least two times with ether. It is best to use ether equal to 12 to 25% of the volume of the water phase. After the ether extraction, the pH of the water phase is brought at least up to 10, preferably by dropwise addition of caustic soda (NaOH), stirred for about 5 minutes, and extracted with an inert solvent at least three times. Benzene or ether are suitable solvents. The extracts are combined and dried over potassium hydroxide or fused potassium sulfate. The compound can be isolated from the solution by removal of the solvent. Alternatively, the compound can be precipitated out of an inert solvent as a salt. Suitable for this process are hydrogen chloride gas or dried hydrogen bromide bubbled through the inert solvent.

In order to convert the secondary amino group into the desired tertiary amine, the secondary amine was treated with aqueous formaldehyde solution, and with concentrated formic acid at an elevated temperature. It is sometimes necessary to reflux for 8 to 12 hours. The aqueous formaldehyde solution consists, for example, of 32% formaldehyde solution, which is a 4- to 8-fold excess (of formaldehyde) based on the quantity of secondary amine to be employed. After the refluxing, the reaction mixture can stand a while at room temperature, preferably overnight. Next, the organic solvent was stripped off and the residue dissolved in NaOH. A 30% solution of NaOH is suitable but other alkalis or other concentrations may be substituted. In any case, the insoluble portion is filtered off and the basic liquid extracted at least three times with an inert solvent such as ether or benzene. The combined extracts are dried over potassium hydroxide or fused potassium sulfate, whereafter the free compound or its salt is isolated.

The following Examples serve to illustrate the discovered process, but in no case limit the discovery.

EXAMPLE 1

1-amino-3,5-dimethyl-adamantane hydrochloride 1.99 grams of 1-chloro-3,5-dimethyl-adamantane were heated with 0.9 gram urea for about 40 minutes at 220° C. The heating was carried out in a closed vessel in an oil bath with a thermostat. After cooling, the reaction product was pulverized and made into a paste with 50 ml. water. The water phase was brought to a pH between 3 and 5 by dropwise addition of concentrated HCl. The acidified water phase was extracted with two 10-ml. ether portions. Next the water phase was brought to a pH between 12 and 13 by addition of sodium hydroxide, and stirred for 5 minutes. After stirring, the alkaline water phase was extracted with four portions of ether, 10 ml. each. The combined ether extracts were dried over potassium hydroxide. By bubbling dried hydrogen chloride through the solution, 1-amino-3,5-dimethyl-adamantane hydrochloride was precipitated. The yield was 1.7 grams (78% of the theoretical yield). The product did not melt until 300° C.

1-amino-3,5-dimethyl-adamantane hydrobromide

Dried hydrogen bromide gas was bubbled through the dried ether solution of 1-amino-3,5-dimethyl-adamantane. The 1-amino-3,5-dimethyl-adamantane hydrobromide precipitated.

1-amino-3,5-dimethyl-adamantane sulfate

The dried ether solution of 1-amino-3,5-dimethyl-adamantane was treated with 0.5 gram concentrated sulfuric acid (H$_2$SO$_4$) in an ice bath, shaken, and the ether distilled. The oily residue was crystallized from hot water. Yield: 1.81 grams (80% of the theoretical yield).

EXAMPLE 2

1-N-methylamino-3,5-dimethyl-adamantane hydrochloride 2.43 grams of 1-bromo-3,5-dimethyl-adamantane was heated with 1.36 grams of N,N'-dimethylurea for 35 minutes at 160° C. The warming was performed in a closed container in an oil bath with a thermostat. The cooled reaction product was treated with water, and the 1-N-methylamino-3,5-dimethyl-adamantane hydrochloride isolated as described in Example 1.

Yield: 1.41 grams (72% of theoretical yield)
Melting point: 257° C.

EXAMPLE 3

1-amino-3-methyl,5-ethyl-adamantane hydrochloride 2.57 grams of 1-bromo-3-methyl,5-ethyl-adamantane was heated with 1.0 gram urea for 20 minutes at 190° C. The heating was done in a thermostatically controlled oil bath. After cooling, the reaction product was worked up as described in Example 1. This produced 1.67 grams of 1-amino-3-methyl,5-ethyl-adamantane hydrochloride. (73% of the theoretical yield).

EXAMPLE 4

1-amino-3,5-di-isopropyl-adamantane hydrochloride 3.0 Grams of 1-bromo-3,5-di-isopropyl-adamantane was heated with 1.0 gram of urea in a closed vessel for 120 minutes at 150° C. After cooling, the reaction product was worked up as described in Example 1. This gave 2.0 grams of 1-amino-3,5-di-isopropyl-adamantane hydrochloride (72% of the theoretical yield).

EXAMPLE 5

1-amino-3,5-di-n-butyl-adamantane hydrochloride 3.27 grams of 1-bromo-3,5-di-n-butyl-adamantane were warmed with 1.2 grams of urea for 160 minutes at 165° C. The heating was performed in a closed vessel in a thermostatically controlled oil bath. After cooling, the reaction product was suspended in 50 ml. water. The water phase was brought to a pH of about 4 through dropwise addition of concentrated hydrochloric acid. The water phase was then extracted with two 10-ml. portions of ether, and brought to a pH of about 13 by dropwise addition of sodium hydroxide. The alkaline solution was stirred for about 10 minutes, after which the aqueous alkaline phase was extracted with four 10-ml. portions of benzene. The combined benzene extracts were dried over fused potassium sulfate. 1-amino-3,5-di-n-butyl-adamantane hydrochloride was precipitated by exposure to dried hydrogen chloride gas. Yield: 1.86 grams (62% of the theoretical yeild).

EXAMPLE 6

1-N,N-dimethylamino)-3,5-dimethyl-adamantane hydrochloride 1.79 grams of the free secondary amino compound obtained as in Example 1 after evaporation of the ether, was refluxed for 6 hours with 4 ml. of a 33% formaldehyde solution. Next, 4 ml. of concentrated formic acid was added and refluxing continued for four hours. After standing, the volatile components were removed from the reaction product by vacuum, and the dry residue dissolved in sodium hydroxide. The pH of the solution lay between 12 and 13. The aqueous alkaline phase was extracted four times with benzene. The combined benzene extracts were dried over fused potassium sulfate, and the 1-(N,N-dimethylamino)-3,5-dimethyl-adamantane hydrochloride precipitated by addition of dried hydrogen chloride gas. Yield: 1.87 grams (77% of the theoretical yield).

EXAMPLE 7

1(-N-methyl,N-isopropylamino)-3,5-dimethyl-adamantane hydrochloride 2.43 grams of 1-bromo-3,5-dimethyl-adamantane hydrochloride were heated in a closed vessel for 40 minutes at 180° C., with 2.8 grams of N,N'-di-isopropylurea. After cooling, the reaction product was suspended in 50 ml. of water, acidified, and extracted with two 10-ml. portions of ether. Next, the water phase was brought to a pH of between 12 and 13 with sodium hydroxide, stirred for 10 minutes, and extracted with four 10-ml. portions of benzene. The benzene extracts were combined, the benzene stripped off, and the residue refluxed for 10 hours with 4 ml. of a 32% formaldehyde solution and 4 ml. of concentrated formic acid. After cooling, the solution was worked up as in Example 6. It yielded 1.04 grams of 1-(N-methyl,N-isopropylamino)-3,5-dimethyl-adamantane hydrochloride. Yield: 38% of theoretical yield.

EXAMPLE 8

1-N-cyclohexyl-3,5-dimethyl-adamantane hydrochloride 2.43 grams of 1-bromo-3,5-dimethyl adamantane and 1.86 grams of N,N'-dicyclohexylurea were heated to 190° C. in a closed vessel for 45 minutes. The cooled product was worked up as in Example 5. 1.52 Grams of 1-N-cyclohexylamino-3,5-dimethyl-adamantane hydrochloride was isolated. Yield: 51% of the theoretical yield. The substance did not melt until 300° C.

1,3,5-trisubstituted-adamantane compounds, prepared in the discovered manner, are suitable for influencing the central nervous system. Without further proof, it should be accepted that 1,3,5-trisubstituted-adamantane compounds of the type described herein influence catecholamine metabolism, for instance by freeing dopamine or stimulating the receptors. The amino-adamantane compounds described herein represent valuable pharmaceuticals. These compounds can be used as such, or converted into mixtures with other preparations.

It was discovered that the 1,3,5-trisubstituted-adamantane compounds here described are well-suited for treatment of Parkinsonism, and further, for treating other kinds of hyperkinesis, including head tremors, thalamic tension conditions and spastic conditions, and even for the activation of akinetic cerebroorganic conditions. It has been experimentally determined that these central nervous system influencing 1,3,5-trisubstituted-adamantane compounds can be dispensed orally or injected, for instance, in the form of an isotonic salt solution, in the form of tablets, sugar-coated pills, gelatin capsules, and the like. In some cases it is recommended to employ the active compound in the form of a sparingly-soluble salt, in order to influence the resorption speed.

As already established, the action of amino-adamantane hydrochloride on the central nervous system is already known. The following investigation verifies the superiority of 1-amino-3,5-dimethyl-adamantane hydrochloride, chosen from among the various preparations discovered, over the known amino-adamantane hydrochloride. Investigated were:
1. The influence upon Spiroperidol Catalepsy, and
2. The antagonism against reserpine sedation (arrest of motility). In the following Tables, D1 stands for amino-adamantine hydrochloride, and D145 stands for 1-amino-3,5-dimethyl-adamantane hydrochloride.

1. Spiroperidol-Catalespy

The cataleptic study was performed on Wistar rats. The Spiroperidol was employed at 0.4 mg/kg (intraperitoneally). Thirty minutes later the substance studied was injected intraperitoneally.

| PREPA-RATION | DOSE mg/kg i.p. | CATALEPSY* x | ± | $S_x$ | P | ANTAGON-ISM |
|---|---|---|---|---|---|---|
| Control | — | 30.0 | ± | 0.0 | — | 0.0 |
| D 1 | 10 | 20.1 | ± | 1.7 | <0.001 | 33.0 |
|  | 20 | 18.9 | ± | 1.7 | <0.001 | 37.0 |
| D 145 | 5 | 27.0 | ± | 1.3 | <0.05 | 10.0 |
|  | 10 | 9.2 | ± | 2.0 | <0.001 | 69.3 |
|  | 20 | 0.4 | ± | 0.3 | <0.001 | 98.7 |

*Average of 8–10 rats

As concluded from the experimental evidence, with the application of 10 or 20 mg/kg of 3,5-dimethyl-adamantyl-1-amino hydrochloride, the Spiroperidol-induced catalepsy was reduced by 69.3% or 98.7%, whereas upon administration of the same amounts of amino-adamantane hydrochloride only 33.0% or 37.0% of the catalepsy was eliminated.

2. Reserpine Sedation

The antagonism against reserpine was tested on Swiss Albino mice. Reserpine (5 mg/kg subcutaneous) was administered 18 hours before the test. The motility was measured with an Animex motility determining apparatus.

| PREPARATION | DOSE mg/kg i.p. | MOTILITY* x | ± | $S_x$ | P |
|---|---|---|---|---|---|
| D 1 | 20 | 16.5 | ± | 4.7 | <0.01 |
|  | 40 | 30.1 | ± | 7.1 | <0.01 |
| D 145 | 10 | 29.8 | ± | 20.0 | >0.2 |
|  | 20 | 50.4 | ± | 39.6 | >0.2 |
|  | 40 | 111.9 | ± | 44.5 | <0.05 |

*Number of Impulses - Averages from 10 mice

As this investigation of the antagonism of Reserpine sedation showed, under standardized conditions, after the application of 40 mg/kg of 3,5-dimethyl-adamantane-1-amino hydrochloride, a motility of 111.9 ± 44.5 impulses was measured, while application of the same amount of amino-adamantane hydrochloride permitted a motility of only 30.1 ± 7.1 impulses.

These results of the investigation unequivocally prove that 3,5-dimethyl-adamantyl-1-amino-hydrochloride exerts a much stronger influence on the central nervous system than amino-adamantane hydrochloride.

We claim:
1. A composition which influences the central nervous system and is especially useful in the treatment of hyperkinesis, having an active ingredient an effective antihyperkinesic amount of 1-amino-3, 5-dimethyl-adamantane or a pharmaceutically acceptable salt thereof, together with a pharmaceutically-acceptable carrier therefor.
2. A composition of claim 1 wherein the salt is the hydrochloride.
3. A method of treating a living mammalian body suffering from hyperkinesis comprising the step of administering an anti-hyperkinesically effective amount of a composition of claim 1 to said mammalian body.
4. A method of treating a living mammalian body suffering from hyperkinesis comprising the step of administering an anti-hyperkinesically effective amount of a composition of claim 2 to said mammalian body.

UNITED STATES PATENT AND TRADEMARK OFFICE
CERTIFICATE OF CORRECTION

PATENT NO. : 4,122,193
DATED : October 24, 1978
INVENTOR(S) : Scherm et al.

It is certified that error appears in the above-identified patent and that said Letters Patent are hereby corrected as shown below:

[56] References Cited, U.S. Patent Documents; "Narayama" should read --Narayanan-- Attachment to Paper 12.
[56] References Cited, Foreign Patent Documents; "9/1970" should read --9/1968-- Attachment to Paper 12.
Col. 5, line 57; "yeild" should read --yield--
Col. 5, line 59; "1-N,N" should read --1-(N,N--
Col. 8, line 27; "an" should read --as-- Response and Amendment dated April 19, 1978, page 1.

Signed and Sealed this

Sixth Day of February 1979

[SEAL]

Attest:

RUTH C. MASON
Attesting Officer

DONALD W. BANNER
Commissioner of Patents and Trademarks